(12) United States Patent
Giroud et al.

(10) Patent No.: US 7,919,106 B2
(45) Date of Patent: Apr. 5, 2011

(54) COSMETIC COMPOSITIONS COMPRISING AT LEAST ONE CARBOXYLIC ANIONIC SURFACTANT AND AT LEAST ONE VINYLAMIDE/VINYLAMINE COPOLYMER, AND PROCESSES OF USE THEREOF

(75) Inventors: Franck Giroud, Chamoux sur Gelon (FR); Laurence Paul, Saint leu la Foret (FR); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 406 days.

(21) Appl. No.: 12/078,583

(22) Filed: Apr. 2, 2008

(65) Prior Publication Data

US 2008/0267897 A1    Oct. 30, 2008

Related U.S. Application Data

(60) Provisional application No. 60/907,566, filed on Apr. 9, 2007.

(30) Foreign Application Priority Data

Apr. 2, 2007    (FR) ..................... 07 54207

(51) Int. Cl.
*A61K 8/02*    (2006.01)
(52) U.S. Cl. ..................................... 424/401
(58) Field of Classification Search ........................ None
See application file for complete search history.

(56) References Cited

U.S. PATENT DOCUMENTS

| 2,528,378 | A | 10/1950 | Mannheimer |
| 2,781,354 | A | 2/1957 | Mannheimer |
| 4,713,236 | A | 12/1987 | Hoover et al. |
| 5,632,977 | A | 5/1997 | Chandran et al. |
| 6,423,305 | B1 | 7/2002 | Cauwet-Martin et al. |
| 2006/0233733 | A1 | 10/2006 | Beauquey et al. |
| 2006/0286057 | A1 | 12/2006 | Cannell et al. |

FOREIGN PATENT DOCUMENTS

| DE | 195 40 853 A1 | 5/1997 |
| DE | 10 2005 014 293 A1 | 9/2006 |
| EP | 1 707 240 A1 | 10/2006 |
| FR | 2 773 069 A1 | 7/1999 |
| WO | WO 96/03969 A1 | 2/1996 |
| WO | WO 2007/003784 A1 | 1/2007 |

OTHER PUBLICATIONS

French Search Report for FR 0754207, dated Nov. 13, 2007.
M.R. Porter, BSc, PhD, CChem, MRSC, "Handbook of Surfactants," Blackie & Son Ltd., Glasgow & London, pp. 116-178 (1991).
English language abstract of DE 195 40 853 A1, May 7, 1997.
English language abstract of DE 10 2005 014 293 A1, Sep. 28, 2006.

*Primary Examiner* — Andrew D Kosar
(74) *Attorney, Agent, or Firm* — Finnegan, Henderson, Farabow, Garrett & Dunner, LLP

(57) ABSTRACT

Disclosed herein are cosmetic compositions comprising:
  at least one carboxylic anionic surfactant, and
  at least one vinylformamide/vinylformamine copolymer comprising from 10 to 90 mol % of units of formula A:

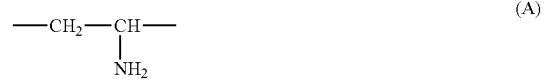

and from 90 to 10 mol % of units of formula B:

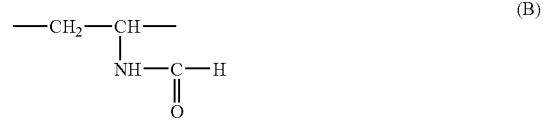

and processes for use thereof.

26 Claims, No Drawings

COSMETIC COMPOSITIONS COMPRISING AT LEAST ONE CARBOXYLIC ANIONIC SURFACTANT AND AT LEAST ONE VINYLAMIDE/VINYLAMINE COPOLYMER, AND PROCESSES OF USE THEREOF

This application claims benefit of U.S. Provisional Application No. 60/907,566, filed Apr. 9, 2007, the contents of which are incorporated herein by reference. This application also claims benefit of priority under 35 U.S.C. §119 to French Patent Application No. FR 0754207, filed Apr. 2, 2007, the contents of which are also incorporated herein by reference.

Disclosed herein are compositions comprising at least one carboxylic anionic surfactant and at least one vinylamide/vinylamine copolymer.

It is known practice to use polymers in the cosmetic field, such as in hair care in leave-in products, for example to give the head of hair hold or styling.

In the field of "rinse-out" hair compositions, such as shampoos or hair conditioners, water-soluble synthetic cationic polymers, which have been known to give the hair a good cosmeticity, are also used; however, these polymers provide no hair shaping effect. This is likewise the case for cationic nature-derived polymers such as modified guar gums, which may also provide a cosmetic nature without allowing hair shaping. In the field of rinse-out compositions, polymers may not provide sufficient styling associated with an acceptable cosmeticity.

Thus, one aspect of the present disclosure is to provide cosmetic compositions comprising polymers capable of providing a real styling effect while at the same time maintaining an acceptable cosmeticity for the compositions.

International Patent Application Publication No. WO 96/03969 describes shampoo compositions containing polyvinylformamides. However, these polymers may not make it possible to obtain a lasting hold.

U.S. Pat. No. 4,713,236 describes shampoo compositions containing polyvinylformamines and an anionic sulphate surfactant. However, these polymers may not make it possible to obtain a lasting hold.

Patent Application Publication Nos. U.S. 2006/286057, WO 2007/003784 and DE 102005014293 disclose compositions comprising vinylamine/vinylamide copolymers, but containing no carboxylic anionic surfactants.

Patent Application Publication Nos. EP-A-1 707 240 and FR-A-2 773 069 disclose shampoo compositions comprising at least one carboxylic anionic surfactant, but containing no vinylamine/vinylamide copolymers.

After considerable research, the inventors have discovered, surprisingly, that the use of the combination of at least one vinylformamide/vinylformamine copolymer as defined hereinafter and of at least one carboxylic anionic surfactant can allow the preparation of rinse-out compositions having real properties of lasting form retention and good cosmetic properties.

Accordingly, one aspect of the present disclosure is the cosmetic compositions comprising, in a cosmetically acceptable medium:

at least one carboxylic anionic surfactant, and
at least one vinylformamide/vinylformamine copolymer comprising from 10 to 90 mol % of units of formula A:

and from 90 to 10 mol % of units of formula B:

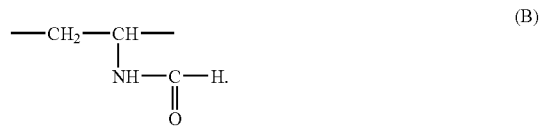

Surprisingly, the compositions according to the disclosure can have beneficial cosmetic properties, for example when applied in a formulation of shampoo type, it has in fact been found that the hair exhibits good cosmetic properties, such as disentangling, smoothing and softness. The compositions according to the present disclosure may make it possible to obtain, once the hair is dried, a shaping of the hair and a hold of this shaping that is beneficial and noticeable.

Another aspect of the present disclosure is also the cosmetic use of the above compositions for cleansing and/or removing makeup from and/or conditioning keratin materials such as the hair and the skin. A further aspect of the disclosure is the use of the composition according to the disclosure as a shampoo for keratin materials.

Carboxylic Anionic Surfactant(s):

According to the present disclosure, the at least one carboxylic anionic surfactant is an anionic surfactant comprising at least one carboxylic functional group (—COOH) optionally in salt form (—COO⁻).

The at least one carboxylic anionic surfactant may comprise no sulphate or sulphonate functional groups and may, for example, be chosen from alkyl D-galactosiduronic acids and salts thereof, polyoxyalkylenated ($C_6$-$C_{24}$)alkyl ether carboxylic acids, polyoxyalkylenated ($C_6$-$C_{24}$)alkylaryl ether carboxylic acids and salts thereof, polyoxyalkylenated ($C_6$-$C_{24}$)alkylamido ether carboxylic acids and salts thereof, for example those containing from 2 to 50 alkylene oxide groups, such as ethylene oxide groups, such as the compounds sold by the company Kao under the name Akypo, ($C_6$-$C_{24}$)acyl sarcosinates and salts thereof, ($C_6$-$C_{24}$)acyl lactylates and salts thereof, and ($C_6$-$C_{24}$)acyl glutamates. ($C_6$-$C_{24}$)alkylpolyglycoside carboxylic esters such as alkylglucoside acetates, alkylglucoside citrates and alkylpolyglycoside tartrate may also be used. Such products are, for example, sold under the names EUCAROL APG/EC and EUCAROL APG/ET by the company Lamberti, and Plantapon LGC Sorb by the company Cognis.

Mixtures of these surfactants may also be used.

The salts can be chosen from, for example, alkali metal salts, such as alkali metal salts of sodium, ammonium salts, amine salts, salts of amino alcohols such as triethanolamine or monoethanolamine, and magnesium salts.

The anionic surfactants of the polyoxyalkylenated carboxylic ether acid or salt type can be chosen from, for example, but not by way of limitation, those of formula (I):

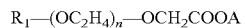

wherein:

$R_1$ is chosen from linear and branched $C_8$-$C_{22}$ alkyl and alkenyl radicals, ($C_8$-$C_9$)alkylphenyl radicals, radicals $R_2CONH—CH_2—CH_2—$ wherein $R_2$ is chosen from linear and branched $C_9$-$C_{21}$ alkyl and alkenyl radicals;

n is an integer or decimal number (average value) ranging from 2 to 24, such as from 2 to 10, the alkyl radical comprising from 6 to 20 carbon atoms approximately, such as from 8 to 18 carbon atoms, and aryl, for example, denoting phenyl;

and A is chosen from H, ammonium, Na, K, Li, Mg and monoethanolamine and triethanolamine residues. Mixtures of compounds of formula (I) may also be used, for example, mixtures in which the groups $R_1$ are different.

In one embodiment, the oxyalkylenated ether carboxylic acids or salts thereof according to the present disclosure are chosen from those of formula (I) wherein $R_1$ is chosen from ($C_{12}$-$C_{14}$)alkyl, cocoyl and oleyl radicals or mixtures of radicals and nonylphenyl or octylphenyl radicals; A denotes a hydrogen or sodium atom; and n ranges from 2 to 20, for example from 2 to 10.

In one embodiment, polyoxyalkylenated ($C_6$-$C_{24}$)alkyl ether carboxylic acids and salts thereof, polyoxyalkylenated ($C_6$-$C_{24}$)alkylamido ether carboxylic acids, such as those comprising from 2 to 15 alkylene oxide groups, and salts thereof, and mixtures thereof, are used.

In another embodiment, compounds of formula (I) are used wherein R denotes a ($C_{1-2}$)alkyl radical, A denotes a hydrogen or sodium atom, and n ranges from 2 to 10.

Examples of the commercial products that may be used include, but are not limited to, the products sold by the company Chem Y under the names:

AKYPO® NP 70 (R=nonylphenyl, n=7, p=0, A=H),
AKYPO® NP 40 (R=nonylphenyl, n=4, p=0, A=H),
AKYPO® OP 40 (R=octylphenyl, n=4, p=0, A=H),
AKYPO® OP 80 (R=octylphenyl, n=8, p=0, A=H),
AKYPO® OP 190 (R=octylphenyl, n=19, p=0, A=H),
AKYPO® RLM 38 (R=($C_{12}$-$C_{14}$)alkyl, n=3.8, p=0, A=H),
AKYPO® RLM 38 NV (R=($C_{12}$-$C_{14}$)alkyl, n=4, p=0, A=Na),
AKYPO® RLM 45 (R=($C_{12}$-$C_{14}$)alkyl, n=4.5, p=0, A=H),
AKYPO® RLM 45 NV (R=($C_{12}$-$C_{14}$)alkyl, n=4.5, p=0, A=Na),
AKYPO® RLM 100 (R=($C_{12}$-$C_{14}$)alkyl, n=10, p=0, A=H),
AKYPO® RLM 100 NV (R=($C_{12}$-$C_{14}$)alkyl, n=10, p=0, A=Na),
AKYPO® RLM 130 (R=($C_{12}$-$C_{14}$)alkyl, n=13, p=0, A=H), and
AKYPO® RLM 160 NV (R=($C_{12}$-$C_{14}$)alkyl, n=16, p=0, A=Na), or those sold by the company Sandoz under the names:
SANDOPAN DTC-Acid (R=($C_{1-3}$)alkyl, n=6, p=0, A=H),
SANDOPAN DTC (R=($C_{13}$)alkyl, n=6, p=0, A=Na),
SANDOPAN LS 24 (R=($C_{12}$-$C_{14}$)alkyl, n=12, p=0, A=Na), and
SANDOPAN JA 36 (R=($C_{13}$)alkyl, n=18, p=0, A=H), and the products sold under the following names:
AKYPO® RLM 45,
AKYPO® RLM 100, and
AKYPO® RLM 38.

In one embodiment, polyoxyalkylenated ($C_6$-$C_{24}$)alkyl ether carboxylic acids and salts thereof, polyoxyalkylenated ($C_6$-$C_{24}$)alkylamido ether carboxylic acids and salts thereof, such as those comprising from 2 to 15 alkylene oxide groups, and ($C_{6-24}$)alkylpolyglycoside carboxylic esters, and salts thereof, and mixtures thereof, are used.

The at least one carboxylic anionic surfactant is generally present in an amount ranging from 0.1% to 40% by weight relative to the total weight of the composition, such as from 0.5 to 25% by weight, or from 0.5% to 15% by weight, or from 1% to 10% by weight.

Vinylformamide/Vinviformamine Copolymer

In one embodiment, the at least one vinylamine/vinylamide copolymer according to the disclosure comprises from 10 to 60 mol % of units of formula A, such as from 20 to 40 mol %.

In another embodiment, the at least one vinylamine/vinylamide copolymer according to the disclosure comprises from 30 to 90 mol % of units of formula B, such as from 60 to 80 mol %.

The copolymers according to the disclosure can be obtained by partial hydrolysis of polyvinylformamide. The hydrolysis can be carried out in an acidic or basic medium.

The at least one vinylamine/vinylamide copolymer according to the present disclosure can optionally comprise at least one additional monomer unit. In this case, the at least one additional monomer units can be present in a total amount of less than 20 mol % of the copolymer.

In one embodiment, the at least one vinylamine/vinylamide copolymer according to the present disclosure is constituted solely of units A and units B.

The weight-average molecular weight, measured by light diffraction, can range from 10,000 to 30,000,000 g/mol, such as from 40,000 to 1,000,000, or from 100,000 to 500,000 g/mol.

The cationic charge density of the at least one vinylamine/vinylamide copolymer at pH 5 can range from 2 meq/g to 20 meq/g, such as from 2.5 to 15 or from 3.5 to 10 meq/g.

Among the vinylamine/vinylamide copolymers that can be used according to the present disclosure, non-limiting mention may be made of LUPAMIN 9030 and 9010 provided by the company BASF.

The at least one vinylamine/vinylamide copolymer is present in the composition according to the present disclosure in an amount ranging from 0.01% to 20% by weight relative to the total weight of the composition, such as from 0.05% to 10% by weight or from 0.1% to 5% by weight.

The compositions according to the present disclosure may also comprise at least one additional surfactant such as, for example, anionic surfactants (different from the carboxylic surfactants), non-ionic surfactants, amphoteric surfactants or zwitterionic surfactants, and mixtures thereof.

In one embodiment, the at least one additional surfactant is chosen from non-ionic surfactants and amphoteric surfactants.

Non-ionic surfactants are compounds known per se (in this regard, see for example "Handbook of Surfactants" by M. R. Porter, Blackie & Son publications (Glasgow and London), 1991, pp. 116-178): they can, for example, but not by way of limitation, be chosen from polyethoxylated polypropoxylated or polyglycerolated fatty alcohols, polyethoxylated, polypropoxylated or polyglycerolated fatty alpha-diols, polyethoxylated, polypropoxylated or polyglycerolated alkylphenols or polyethoxylated, polypropoxylated or polyglycerolated fatty acids, having a fatty chain comprising, for example, 8 to 18 carbon atoms, it being possible for the number of ethylene oxide or propylene oxide groups to range from 2 to 50, and it being possible for the number of glycerol groups to range from 2 to 30. Non-limiting mention may also be made of copolymers of ethylene oxide and of propylene oxide, condensates of ethylene oxide and of propylene oxide with fatty alcohols; polyethoxylated fatty amides, for example those comprising from 2 to 30 mol of ethylene oxide, polyglycerolated fatty amides comprising, on average, from 1 to 5 glycerol groups, such as from 1.5 to 4; polyethoxylated fatty amines, such as those comprising from 2 to 30 mol of ethylene oxide; oxyethylenated sorbitan fatty acid esters comprising from 2 to 30 mol of ethylene oxide; sucrose fatty acid esters, polyethylene glycol fatty acid esters, alkylpolyglycosides, N-alkylglucamine derivatives, amine oxides such as $(C_{10}$-$C_{14})$alkylamine oxides or N-acylaminopropylmorpholine oxides. For example, the at least one additional surfactant can be a nonionic surfactant chosen from alkylpolyglycosides.

As regards the alkylpolyglycosides, these compounds are known and can be, for example, chosen from those of formula (I):

$$R_1O-(R_2O)_t(G)_v \qquad (I)$$

wherein $R_1$ is chosen from linear and branched alkyl and/or alkenyl radicals comprising approximately from 8 to 24 carbon atoms, and alkylphenyl radicals wherein the linear or branched alkyl radical comprises from 8 to 24 carbon atoms, $R_2$ is an alkylene radical comprising approximately from 2 to 4 carbon atoms, G is a sugar unit comprising 5 or 6 carbon atoms, t is a value ranging from 0 to 10, such as from 0 to 4, and v is a value ranging from 1 to 15.

In one embodiment, alkylpolyglycosides according to the present disclosure are chosen from compounds of formula (I) wherein $R_1$ is chosen from linear and branched, saturated and unsaturated alkyl radicals comprising from 8 to 18 carbon atoms, t is a value ranging from 0 to 3, such as equal to 0, and G is chosen from glucose, fructose and galactose, for example glucose. The degree of polymerization, i.e. the value of v in formula (I), can range from 1 to 15, such as from 1 to 4. In one embodiment, the average degree of polymerization ranges from 1 to 2, such as from 1.1 to 1.5.

The glycosidic linkages between the sugar units are of 1-6 or 1-4 type, for example 1-4 type.

Compounds of formula (I) ca be, for example, represented by the products sold by the company Cognis under the names PLANTAREN® (600 CS/U, 1200 and 2000) or PLANTACARE® (818, 1200 and 2000). In another embodiment, use may also be made of the products sold by the company Seppic under the names TRITON CG 110 (or ORAMIX CG 110) and TRITON CG 312 (or ORAMIX® NS 10), the products sold by the company BASF under the name LUTENSOL GD 70 or else those sold by the company ChemY under the name AG10 LK.

Use may also be made, for example, of the alkyl(C8/C16) polyglucoside (1,4) in aqueous solution at 53% sold by Cognis under the reference PLANTACARE® 818 UP.

In one embodiment, the at least one non-ionic surfactant is chosen from alkylpolyglycosides, such as $(C_6$-$C_{24})$alkylpolyglucosides, or $(C_8$-$C_{16})$alkylpolyglucosides.

The non-ionic surfactants may be present in an amount ranging from 0.1% to 25% by weight, such as from 1% to 15% by weight, relative to the total weight of the composition.

As regards the amphoteric or zwitterionic surfactants, non-limiting mention may be made, of aliphatic secondary or tertiary amine derivatives wherein the aliphatic radical is a linear or branched chain comprising from 8 to 18 carbon atoms and comprising at least one water-solubilizing anionic group (for example, carboxylate, sulphonate, sulphate, phosphate or phosphonate); non-limiting mention may also be made of $(C_8$-$C_{20})$alkyl betaines, sulphobetaines, $(C_8$-$C_{20})$ alkylamido$(C_1$-$C_6)$alkyl betaines or $(C_8$-$C_{20})$alkylamido$(C_1$-$C_6)$alkyl sulphobetaines.

Among amine derivatives, non-limiting mention may be made of the products sold under the name MIRANOL, as described in U.S. Pat. Nos. 2,528,378 and 2,781,354 and categorized in the CTFA dictionary, 3rd edition, 1982, under the names Amphocarboxyglycinates and Amphocarboxypropionates having the respective structures:

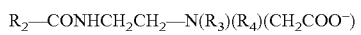

wherein: $R_2$ is an alkyl radical of an acid $R_2$—COOH present in hydrolyzed coconut oil or a heptyl, nonyl or undecyl radical, $R_3$ denotes a beta-hydroxyethyl group and $R_4$ denotes a carboxymethyl group;
and

wherein:
(B) is —CH$_2$CH$_2$OX', (C) is —(CH$_2$)$_z$—Y', with z=1 or 2,
X' denotes the group —CH$_2$CH$_2$—COOH or a hydrogen atom,
Y' denotes —COOH or the radical —CH$_2$—CHOH—SO$_3$H,
$R_2$' is chosen from alkyl radicals of an acid $R_2$'—COOH present in hydrolyzed linseed oil or coconut oil, alkyl radicals, such as $C_7$, $C_9$, $C_{11}$ or $C_{13}$ alkyl radicals, $C_{1-7}$ alkyl radicals and their iso forms, and unsaturated $C_{17}$ radicals.

These compounds are categorized in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylampho-dipropionate, Disodium Capryloamphodipropionate, Lauroamphodipropionic Acid, Cocoamphodipropionic Acid, Disodium Cocoamphocarboxy Ethyl Hydroxypropyl Sulphonate.

By way of example, non-limiting mention may be made of the cocoamphodiacetate sold under the trade name MIRANOL® C2M concentrate by the company Rhodia Chimie.

The compositions according to the disclosure can also comprise anionic surfactants different from the carboxylic anionic surfactants.

By way of example, but not by way of limitation, of anionic surfactants that can be used, alone or as a mixture, in the context of the present disclosure, mention maybe made of salts (such as alkaline salts, for example sodium salts, ammonium salts, amine salts, amino alcohol salts or magnesium salts) of the following compounds: alkyl sulphates, alkyl ether sulphates, alkylamido ether sulphates, alkylaryl polyether sulphates, monoglyceride sulphates; alkylsulphonates, alkyl phosphates, alkylamidesulphonates, alkylarylsulphonates, α-olefin sulphonates, paraffin sulphonates; and alkyl ether phosphates.

In combination with the carboxylic anionic surfactants, the at least one anionic surfactant suitable for the compositions according to the present disclosure can be, in one embodiment, chosen from sodium lauryl ether sulphate, ammonium lauryl ether sulphate, sodium lauryl sulphate or ammonium lauryl sulphate, and/or mixtures thereof.

If at least one additional surfactant is present, then the content of additional surfactant(s) ranges from 0.1% to 25% by weight relative to the total weight of the composition, such as from 1% to 15% by weight or from 1.5% to 10% by weight relative to the total weight of the composition.

The compositions according to the disclosure can comprise a total concentration of surfactants ranging from 4% to 50% by weight relative to the total weight of the composition, such as from 8% to 30% by weight.

The composition according to the disclosure can further comprise at least one additional conditioning agent different from the at least one vinylamine/vinylamide copolymer.

When the composition contains at least one additional conditioning agent, it is generally chosen from synthetic oils, such as poly-α-olefins, fluorinated oils, fluorinated waxes, fluorinated gums, non-fluorinated waxes, fatty esters of carboxylic acids, cationic polymers, silicones, mineral, plant or animal oils, ceramides and pseudoceramides, and mixtures thereof.

According to one embodiment, the at least one additional conditioning agent is chosen from cationic polymers different from the at least one vinylamine/vinylamide copolymer of the disclosure and silicones. In one embodiment, the at least one additional conditioning agent is chosen from silicones, such as non-volatile silicones.

According to this embodiment, the content of additional conditioning agent in the composition according to the disclosure ranges from 0.001% to 25% by weight relative to the total weight of the final composition, such as from 0.005% to 10% by weight or from 0.01% to 5% by weight.

The cationic polymer(s) is (are) generally present at concentrations ranging from 0.01% to 20% by weight relative to the total weight of the composition, such as from 0.05% to 10% or from 0.1% to 5% by weight.

By way of silicones that can be used in the compositions of the present disclosure, non-limiting mention may be made of volatile or non-volatile, cyclic or acyclic, branched or unbranched and organomodified or non-organomodified silicones.

The silicones that can be used in accordance with the disclosure may be soluble or insoluble in the composition, and may, for example, be polyorganosiloxanes which are insoluble in the composition of the disclosure; they may be in the form of oils, waxes, resins or gums.

In one embodiment, the silicones are chosen from non-ionic polydimethylsiloxanes comprising trimethylsilyl end groups or dimethylsilanol end groups (dimethicone or dimethiconol according to the INCI nomenclature).

According to the disclosure, all the silicones may be used as-is, or in the form of solutions, dispersions, emulsions, nanoemulsions or microemulsions.

The silicones may be used alone or as a mixture, in an amount ranging from 0.01% to 20% by weight relative to the total weight of the composition, for example from 0.1% to 5% by weight.

The composition according to the present disclosure may also comprise at least one adjuvant commonly used in cosmetics, such as vitamins, fragrances, pearlescent agents, thickeners, polymers different from the at least one vinylformamide/vinylformamine copolymer of the present disclosure, gelling agents, trace elements, softeners, sequestering agents, basifying or acidifying agents, preservatives, sunscreens, antioxidants, agents for combating hair loss, antidandruff agents, agents for combating fat, free-radical scavengers, and mixtures thereof. Of course, those skilled in the art would take care to choose this or these possible additional compound(s) and/or the amounts thereof in such a way that the beneficial properties of the composition according to the disclosure are not, or are not substantially, impaired by the envisaged addition.

In one embodiment, the pH of the composition of the present disclosure ranges from 2 to 11, such as from 3 to 10, for example from 5 to 8.

The cosmetically acceptable medium comprises at least one constituent chosen from water and hydrophilic organic solvents such as alcohols, for example, linear or branched $C_1$-$C_6$ monoalcohols, and polyols and glycol ethers.

The composition according to the present disclosure may further comprise at least one propellant. The at least one propellant may be chosen, for example, from the compressed or liquefied gases commonly used in the preparation of aerosol compositions and mixtures thereof. In one embodiment, use is made of air, carbon dioxide or nitrogen which is compressed or else a soluble gas, such as dimethyl ether, halogenated (such as fluorinated) or non-halogenated hydrocarbons, and mixtures thereof.

In one embodiment, the compositions of the disclosure are used in the hair care field, such as for the form retention of the hairstyle or the shaping of the hair. The hair compositions are, for example, shampoos, gels, hair setting lotions, blow drying lotions or fixing and styling compositions, such as lacquers or sprays. The lotions may be packaged in various forms, for example in vaporizers or pump-action sprays or in aerosol containers, in order to ensure application of the composition in the vaporized form or in the form of a mousse.

In one embodiment, the compositions in accordance with the present disclosure can be used for washing and treating keratin materials such as the hair, the skin, the eyelashes, the eyebrows, the nails, the lips or the scalp. In another embodiment, the compositions are used for washing and treating the hair.

In one embodiment, the compositions according to the present disclosure are detergent compositions, such as shampoos, shower gels and bubble baths. In this embodiment of the disclosure, the compositions comprise at least one anionic and/or non-ionic detergent surfactant in an amount of at least 4% by weight relative to the total weight of the composition.

Another aspect of the present disclosure is therefore also a process for the treatment of keratin materials such as the skin or the hair, characterized in that it comprises applying to the keratin materials, a cosmetic composition as defined above, and optionally rinsing with water.

Thus, this process according to the disclosure makes it possible to retain the form of the hairstyle or to treat, care for and wash or remove makeup from the skin, the hair or any other keratin material.

In another embodiment, the compositions of the disclosure may be in the form of a rinse-out or leave-in conditioner or in the form of rinse-out compositions to be applied before or after any hair treatment, such as a dyeing operation, a bleaching operation, a permanent waving operation or a hair straightening operation, or else between the two steps of a permanent waving operation or of a hair straightening operation.

In one embodiment, when the composition is in the form of a conditioner that may be optionally rinsed-out, it contains at least one cationic surfactant, for example in an amount ranging from 0.1% to 10% by weight relative to the total weight of the composition, such as from 0.5% to 5% by weight.

The composition according to the disclosure, after application to human hair and the human scalp, may or may not be rinsed out after any treatment. In one embodiment, it is rinsed out. It can be in any form conventionally used in the field in question, and for example in the form of a more or less thickened lotion, of a gel, of a cream, of a spray or of a mousse. This composition may be single-phase or multiphase.

According to one embodiment of the disclosure, the composition may be used as a shampoo.

When the compositions in accordance with the disclosure are used as conventional shampoos, they are simply applied to wet hair and the foam generated by massage or friction with the hands is subsequently removed, after an optional leave-on time, by rinsing with water or with an aqueous composition, it being possible for the operation to be repeated at least one time.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

The percentages are expressed as percentage by weight of active material.

EXAMPLES

The following shampoo compositions were prepared:

These locks were then suspended from a hook, i.e. subjected to their own weight.

After suspending, the initial length ($l_0$) of the coiled lock was measured.

The locks were then conditioned for 24 hours in a glove box at controlled relative humidity and controlled temperature (25° C./45% relative humidity).

After suspending for 24 hours, the length (lt) of the locks, which had relaxed under the action of their own weight, was again measured.

The % of curl form retention was calculated by the following equation:

$$\% \text{ of form retention} = \left[\frac{(l - l_t)}{(l - l_0)}\right] * 100$$

l: length of the lock before coiling
$l_0$: length of the curled lock immediately after suspending
$l_t$: length of the curled lock after suspending for 24 hours The closer the value obtained is to 100%, the more marked and lasting is the shaping of the lock.

| As % AM | Ex. 1 (Inventive) | Ex. 2 | Ex. 3 | Ex. 4 | Ex. 5 | Ex. 6 |
|---|---|---|---|---|---|---|
| Laureth-5 carboxylic acid (Empicol CED 5 FL (Hunstman)) | 1.8 | 1.8 | 1.8 | 1.8 | 1.8 | — |
| Cocoglucoside (Plantacare 818 UP from Cognis) | 11 | 11 | 11 | 11 | 11 | 11 |
| Coco amido propyl betaine (Tego betaine F50 from Degussa) | 2.6 | 2.6 | 2.6 | 2.6 | 2.6 | 2.6 |
| Sodium lauryl ether sulphate | | | | | | 1.8 |
| Vinylformamide/vinylformamine copolymer (70/30 in moles) (Lupamin 9030 from BASF) | 1 | — | — | — | — | 1 |
| Polyvinylformamide (Lupamin 9000 from BASF) | — | 1 | — | — | — | — |
| Polyvinylformamine (Lupamin 9095 from BASF) | — | — | 1 | — | — | — |
| Polyethyleneimine (Lupasol P from BASF) | — | — | — | 1 | — | — |
| Preservative | qs | qs | qs | qs | qs | qs |
| Fragrance | qs | qs | qs | qs | qs | qs |
| pH agent, qs | pH 6.5 | pH 6.5 | pH 6.5 | pH 6.5 | pH 6.5 | pH 6.5 |
| Water, qs | 100 | 100 | 100 | 100 | 100 | 100 |

Evaluation of the Curl Form Retention 1 gram of each formulation was applied to a lock of natural Caucasian hair having a length (l) of approximately 25 cm and weighing 2.7 g.

The locks were massaged, left to stand for 5 minutes, and then rinsed.

The wet locks were then coiled around a curler (Ø=2 cm) and then dried under a hood for 30 minutes at 70° C.

The curlers were removed and a "ringlet" was obtained, i.e. a lock coiled in a spiral of variable length.

| | Ex. 1 (Inventive) | Ex. 2 | Ex. 3 | Ex. 4 | Ex. 6 | Ex. 5 |
|---|---|---|---|---|---|---|
| % curl form retention | 78% | 57% | 63% | 52% | 63% | 50% |

The hair treated with the composition of Example 1 exhibited shaping which was more lasting.

Furthermore, the hair treated with the composition of Example 1 exhibited good disentangling and smoothing properties. It was also soft and shiny.

Aerosol Compositions According to the Disclosure

The following compositions were prepared:

| % AM | Ex. 7 (inventive) | Ex. 8 (inventive) |
|---|---|---|
| Laureth 5 carboxylic acid | 1.8 g | 1.8 g |
| Coco amidopropyl betaine | 2.6 g | 2.6 g |
| Coco glucoside | 11 g | |
| Polyglyceryl-3 hydroxylauryl ether (Chimexane NF from Chimex) | | 11 g |
| Vinylformamide/vinylformamine copolymer (70/30 in moles) (Lupamin 9030 from BASF) | 1 | 1 |
| Preservative | Qs | Qs |
| Fragrance | Qs | Qs |
| pH agent, qs | pH 6.5 | pH 6.5 |
| Isobutane/propane/butane (Propel 45 from Repsol) | 5 g | 5 g |
| Water, qs | 100 g | 100 g |

Examples 9 and 10

The following shampoo compositions according to the present disclosure were prepared:

| As % AM | Ex. 9 (inventive) | Ex. 8 (inventive) |
|---|---|---|
| Laureth-5 carboxylic acid (EMPICOL CED 5 FL (Hunstman)) | 7.3 | 1.8 |
| Coco amido propyl betaine (Tego betaine F50 from Degussa) | 8.1 | 2.6 |
| Vinylformamide/vinyl-formamine copolymer (70/30 in moles) (LUPAMIN 9030 from BASF) | 1 | 1 |
| Polyglyceryl-3 hydroxylauryl ether (CHIMEXANE NF from Chimex) | | 11 |
| Preservative | qs | qs |
| Fragrance | qs | qs |
| Citric acid, qs | pH 5.5 | pH 5.5 |
| Water, qs | 100 | 100 |

What is claimed is:

1. A cosmetic composition, comprising, in a cosmetically acceptable aqueous medium:
   at least one carboxylic anionic surfactant, and
   at least one vinylformamide/vinylformamine copolymer comprising from 10 to 90 mol % of units of formula A:

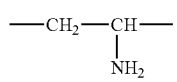

(A)

and from 90 to 10 mol % of units of formula B:

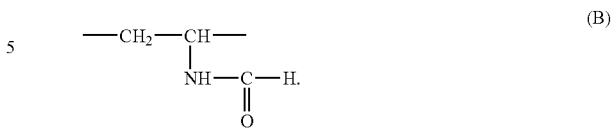

(B)

2. The composition according to claim 1, wherein the at least one carboxylic anionic surfactant is chosen from alkyl D-galactosiduronic acids and salts thereof, polyoxyalkylenated ($C_6$-$C_{24}$)alkyl ether carboxylic acids and salts thereof, polyoxyalkylenated ($C_6$-$C_{24}$)alkylaryl ether carboxylic acids and salts thereof, polyoxyalkylenated ($C_6$-$C_{24}$)alkylamido ether carboxylic acids and salts thereof, ($C_6$-$C_{24}$)acyl sarcosinates and salts thereof, ($C_6$-$C_{24}$)acyl lactylates and salts thereof, ($C_6$-$C_{24}$)acyl glutamates and salts thereof, and ($C_6$-$C_{24}$)alkylpolyglycoside carboxylic esters and salts thereof.

3. The composition according to claim 2, wherein the at least one carboxylic anionic surfactant is chosen from polyoxyalkylenated ($C_6$-$C_{24}$)alkyl ether carboxylic acids, and salts thereof, and polyoxyalkylenated ($C_6$-$C_{24}$)alkylamido ether carboxylic acids, and salts thereof.

4. The composition according to claim 3, wherein the at least one polyoxyalkylenated ($C_6$-$C_{24}$)alkylamido ether carboxylic acid comprises from 2 to 15 alkylene oxide groups.

5. The composition according to claim 1, wherein the at least one carboxylic anionic surfactant is present in the compositions in an amount ranging from 0.1% to 40% by weight relative to the total weight of the composition.

6. The composition according to claim 5, wherein the at least one carboxylic anionic surfactant is present in the compositions in an amount ranging from 1% to 10% by weight.

7. The composition according to claim 1, wherein the at least one vinylamine/vinylamide copolymer comprises from 10 to 60 mol % of units of formula A.

8. The composition according to claim 7, wherein the at least one vinylamine/vinylamide copolymer comprises from 20 to 40 mol % of units of formula A.

9. The composition according to claim 1, wherein the at least one vinylamine/vinylamide copolymer is present in the composition in an amount ranging from 0.01% to 20% by weight relative to the total weight of the composition.

10. The composition according to claim 9, wherein the at least one vinylamine/vinylamide copolymer is present in the composition in an amount ranging from 0.1% to 5% by weight relative to the total weight of the composition.

11. The composition according claim 1, further comprising at least one additional surfactant.

12. The composition according to claim 11, wherein the at least one additional surfactant is chosen from non-ionic surfactants and amphoteric surfactants.

13. The composition according to claim 11, wherein the at least one additional surfactant is present in an amount ranging from 0.1% to 20% by weight, relative to the total weight of the composition.

14. The composition according to claim 1, further comprising at least one additional conditioning agent.

15. The composition according to claim 14, wherein the at least one additional conditioning agent is chosen from poly-α-olefins; fluorinated oils; fluorinated waxes; fluorinated gums; esters of carboxylic acids; silicones; cationic polymers; mineral, plant and animal oils; ceramides; and pseudoceramides.

16. The composition according to claim 15, wherein the at least one additional conditioning agent is chosen from cationic polymers and silicones.

17. The composition according to claim 16, wherein the at least one additional conditioning agent is a silicone.

18. The composition according to claim 16, wherein the at least one additional conditioning agent is a cationic polymer.

19. The composition according to claim 14, wherein the at least one additional conditioning agent is present in a total amount ranging from 0.001% to 25% by weight relative to the total weight of the composition.

20. The composition according to claim 1, further comprising at least one adjuvant chosen from fatty alcohols comprising from 12 to 26 carbon atoms; polymers different from the at least one vinylformamide/vinylformamine copolymer; vitamins, fragrances, pearlescent agents, thickeners, gelling agents, trace elements, softeners, sequestering agents, basifying and acidifying agents, preservatives, sunscreens, antioxidants, agents for combating hair loss, antidandruff agents, agents for combating fat, and propellants.

21. The composition according to claim 1, wherein the cosmetically acceptable medium comprises at least one constituent chosen from water and hydrophilic organic solvents.

22. The composition according to claim 1, wherein the composition is in the form of a hair composition for the form retention of the hairstyle or the shaping of the hair chosen from shampoos; gels; hair setting lotions; blow drying lotions; fixing compositions; styling compositions; rinse-out conditioners; leave-in conditioners; permanent waving compositions; hair straightening compositions; dyeing compositions; bleaching compositions; and rinse-out compositions to be applied before or after a dyeing operation, a bleaching operation, a permanent waving operation or a hair straightening operation, or applied between the two steps of a permanent waving operation or of a hair straightening operation.

23. A composition according to claim 1, wherein the composition is a shampoo for keratin materials.

24. A process for cleansing and/or removing makeup from and/or conditioning keratin materials comprising applying to the makeup and/or keratin materials a composition comprising in a cosmetically acceptable aqueous medium:
at least one carboxylic anionic surfactant, and
at least one vinylformamide/vinylformamine copolymer comprising from 10 to 90 mol % of units of formula A:

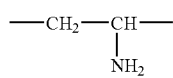

(A)

and from 90 to 10 mol % of units of formula B:

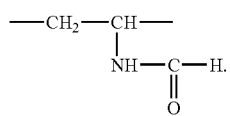

(B)

25. A cosmetic process for the treatment of keratin materials, comprising
applying to the keratin materials a cosmetic composition comprising in a cosmetically acceptable aqueous medium:
at least one carboxylic anionic surfactant, and
at least one vinylformamide/vinylformamine copolymer comprising from 10 to 90 mol % of units of formula A:

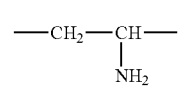

(A)

and from 90 to 10 mol % of units of formula B:

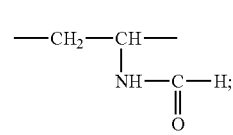

(B)

and optionally rinsing after an optional leave-on time.

26. A process for washing keratin materials, comprising
applying to the keratin materials a composition comprising, in a cosmetically acceptable aqueous medium:
at least one carboxylic anionic surfactant, and
at least one vinylformamide/vinylformamine copolymer comprising from 10 to 90 mol % of units of formula A:

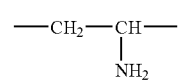

(A)

and from 90 to 10 mol % of units of formula B:

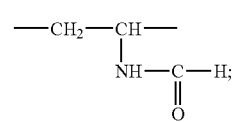

(B)

and then optionally rinsing with water.

* * * * *